(12) United States Patent  
McCullough

(10) Patent No.: US 12,144,758 B1  
(45) Date of Patent: Nov. 19, 2024

(54) THERAPEUTIC FOOT AND ANKLE ALIGNMENT DEVICE

(71) Applicant: Meena McCullough, Euless, TX (US)

(72) Inventor: Meena McCullough, Euless, TX (US)

( * ) Notice: Subject to any disclaimer, the term of this patent is extended or adjusted under 35 U.S.C. 154(b) by 0 days.

(21) Appl. No.: 18/316,699

(22) Filed: Jun. 1, 2023

(51) Int. Cl.
    *A61F 5/00* (2006.01)
    *A61F 5/01* (2006.01)
    *A61H 1/02* (2006.01)

(52) U.S. Cl.
    CPC .......... *A61F 5/019* (2013.01); *A61H 1/0266* (2013.01); *A61H 2001/027* (2013.01); *A61H 2201/1642* (2013.01); *A61H 2201/165* (2013.01)

(58) Field of Classification Search
    CPC ........ A61F 5/019; A61F 5/0195; A61F 5/058; A61F 5/05866; A61F 5/05875; A61F 5/10; A61F 5/14; A61F 5/0111; A61H 1/0266; A61H 1/0285; A61H 1/0288; A61H 1/0218; A61H 1/0229
    USPC .......................................................... 602/30
    See application file for complete search history.

(56) References Cited

U.S. PATENT DOCUMENTS

| | | | | |
|---|---|---|---|---|
| 1,098,397 A * | 6/1914 | Pecorella | ................ | A61F 5/019 128/893 |
| 1,295,611 A * | 2/1919 | Schwartz | ................ | A61F 5/019 200/16 R |
| 1,746,865 A | 2/1930 | George | | |
| 2,016,930 A * | 10/1935 | McCahan | ............ | A61H 1/0266 601/27 |
| 2,367,092 A * | 1/1945 | Blotner | .................. | A43B 3/122 D2/918 |
| 2,506,308 A * | 5/1950 | Maynier | ................ | A45D 29/22 132/73 |
| 4,244,359 A * | 1/1981 | Dieterich | .................. | A43B 7/26 602/30 |
| 4,602,626 A * | 7/1986 | Johnson | ................ | A61F 5/0195 602/27 |
| 4,869,499 A | 9/1989 | Schiraldo | | |
| 7,676,850 B2 * | 3/2010 | Steel | ...................... | A43B 3/105 2/239 |
| 7,784,115 B1 | 8/2010 | Nemcik | | |
| 8,413,349 B2 * | 4/2013 | Krauss | .................... | A61F 5/019 36/94 |
| 8,523,194 B2 | 9/2013 | Smirman | | |
| D707,362 S | 6/2014 | Cohen et al. | | |
| 8,932,186 B2 | 1/2015 | Ferri | | |
| 9,565,889 B2 | 2/2017 | Lazaris | | |
| 9,937,374 B2 | 2/2018 | Leary | | |
| 2004/0103561 A1 | 6/2004 | Campbell et al. | | |
| 2005/0047677 A1 | 3/2005 | Alaimo et al. | | |
| 2005/0101897 A1* | 5/2005 | Froom | .................. | A61F 5/3761 602/21 |
| 2005/0145255 A1* | 7/2005 | Mengato | ............ | A61F 5/05866 128/878 |
| 2010/0249686 A1 | 9/2010 | Rushton | | |
| 2011/0130695 A1* | 6/2011 | Rafique | .................... | A61F 5/14 602/30 |

(Continued)

*Primary Examiner* — Adam Baker

(57) ABSTRACT

A therapeutic footwear device used to stretch the muscles of the foot to assist with correcting and rehabilitating deformities and pain conditions in the feet, legs, and back of the user. The device includes a rigid base which supports the user's foot, straps that spread the user's toes, and inserts and contours that elevate the user's toes to assist in stretch during rest, during exercise performance, and during medical treatment.

19 Claims, 4 Drawing Sheets

(56) References Cited

U.S. PATENT DOCUMENTS

2011/0179674 A1\* 7/2011 Heid ..................... A43B 7/20
 36/11.5
2014/0336012 A1 11/2014 Gourineni
2021/0038420 A1 2/2021 Hanft \* cited by examiner

THERAPEUTIC FOOT AND ANKLE ALIGNMENT DEVICE

BACKGROUND

Medical conditions of the foot, such as foot pain, neuroma, bunions, plantar fasciitis, lateral ankle sprains, and metatarsalgia are suffered by many. A number of therapeutic footwear devices are already known, but these articles fail to activate both the deep and superficial muscles of the foot through extension and maximal abduction of the toes. Furthermore, the existing articles produced are not adjustable. Adjustability allows the device to accommodate users with differing anatomy and allows the user to adjust the device based on their own specific medical needs.

For the foregoing reasons, there is a need for a therapeutic footwear device that is adjustable to accommodate a wide array of users and needs and that uses the full range of motion of the foot to activate the deep and superficial muscles of the foot and to open biomechanical pathways in movement previously inaccessible to the user, creating a therapeutic environment for the entire body.

BRIEF SUMMARY

The present invention is directed towards an apparatus that provides for a therapeutic application of pressure to the foot, which substantially eliminates or reduces disadvantages and problems associated with previous systems and methods.

In some embodiments, the therapeutic footwear device includes a rigid base configured to receive at least a portion of a foot. The top surface of the rigid base includes a sloping contour. The sloping contour receives the four lateral toes and increases in thickness as the contour continues from the lateral edge to the medial edge of the rigid base. The top surface of the rigid base includes a toe retention arrangement. In some embodiments, the toe retention arrangement may be a depression near the medial edge of the rigid base. In some embodiments, the toe retention arrangement may be a medial connection arrangement on the medial edge of the rigid base and a medial adjustable toe retainer connected to the medial connection arrangement. Some embodiments may include both the depression and the medial connection arrangement and medial adjustable toe retainer. The device further includes a lateral connection arrangement on the lateral edge of the rigid. The device further includes a lateral adjustable toe retainer connected to the lateral connection.

In some embodiments, the bottom surface of the rigid base may be substantially ovate.

In some embodiments, the lateral adjustable toe retainer and the medial adjustable toe retainer may each comprise a strap that enters and exits through the nearest connection arrangement.

In some embodiments, the medial connection arrangement may comprise a hole in the medial edge and the lateral connection arrangement may comprise a hole in the lateral edge of the rigid base.

In some embodiments, both ends of the strap of the adjustable toe retainers may connect and separate in a way that allows for tightening or loosening of the adjustable toe retainer.

In certain embodiments, the device may include a cavity on the top surface or bottom surface of the rigid base on the lateral edge and a cavity on the top surface or bottom surface of the rigid base on the medial edge that can house the excess of the strap of the nearest adjustable toe retainers.

In some embodiments, the therapeutic footwear device includes a rigid platform configured to receive at least a portion of the foot. The device further comprises a medial side wall and a lateral side wall that extend upward from the top surface of the rigid platform. The medial side wall and the lateral side wall each have a proximal and a distal connection arrangement. The device further comprises a medial adjustable toe retainer that is connected to the distal connection arrangement on the medial wall and a lateral adjustable toe retainer that is connected to the distal connection arrangement on the lateral wall. The device further comprises an adjustable foot retainer that is connected to the proximal connection arrangements on both the medial side wall and the lateral side wall.

In some embodiments, the lateral and medial adjustable toe retainers may each comprise a strap that enters and exits through the nearest connection arrangement and both ends of the strap pass through an adjustable fastener.

In some embodiments, the adjustable foot retainer may comprise a strap that passes through the proximal connection arrangement on the lateral side wall and through the proximal connection arrangement on the medial side wall. One end of the strap of the adjustable foot retainer may be affixed rigidly to a proximal connection arrangement. The other end of the strap of the adjustable foot retainer may pass through the other proximal connection arrangement and a proximal adjustable fastener.

In some embodiments, the distal connection arrangements and the proximal connection arrangements may comprise a hole in a side wall of the device.

In some embodiments, the strap of the lateral adjustable toe retainer or the strap of the medial adjustable toe retainer may contain an elevated insert that rests under the user's toe.

BRIEF DESCRIPTION OF THE DRAWINGS

These and other features, aspects, and advantages of the present invention will become better understood with regard to the following description, appended claims, and accompanying drawings where:

DETAILED DESCRIPTION

The embodiments of the invention described herein are not intended to be exhaustive or to limit the invention to the precise forms disclosed. Rather, the embodiments selected for description have been chosen to enable one skilled in the art to practice the invention.

Referring to FIGS. 1-8, therapeutic footwear devices 100 and 200 are depicted. Therapeutic footwear devices 100 and 200 are designed to elicit deep stretch responses in the user by activating hard to reach muscles and increasing biomechanical force transmissions through isometric forces and ground reaction forces. Therapeutic footwear devices 100 and 200 are designed to transmit these forces from the joints in the foot and up the leg and back by aligning the body from the feet, all the way up to the hips and back.

Figure 1:
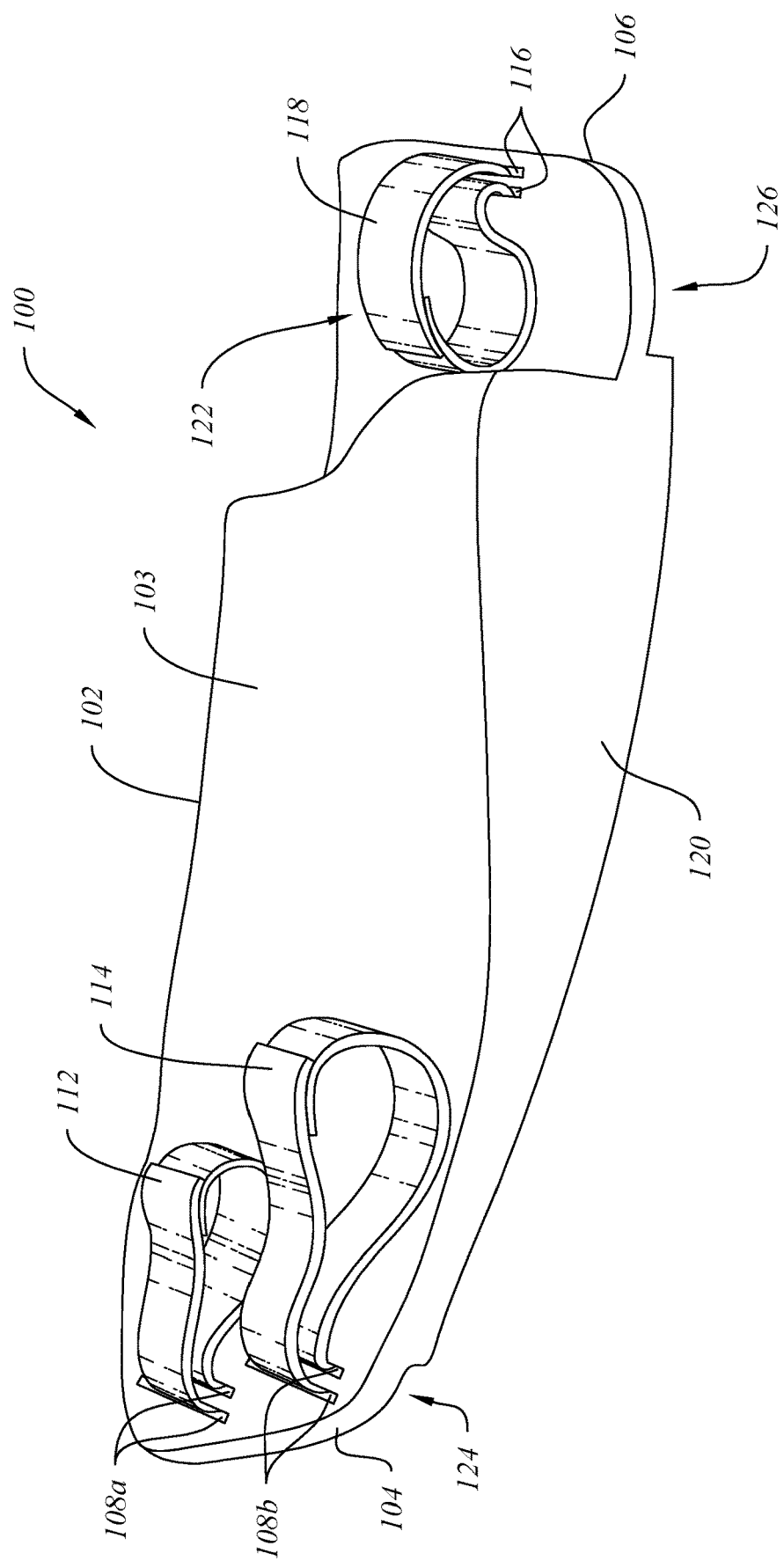
FIG. 1 shows a perspective view of an embodiment of a therapeutic foot and ankle alignment device in accordance with one embodiment of the invention.

As shown in FIG. 1, therapeutic footwear device 100 includes a rigid base 120 that is configured to receive the distal portion of the user's foot. The rigid base comprises a top surface, a bottom surface, a distal edge, a proximal edge 102, a lateral edge 104, and a medial edge 106. While a device for a user's right foot is depicted, a mirror-image device for a user's left foot is contemplated and may also be utilized.

Rigid base 120 is comprised of a material hard enough to resist permanent deformation under the weight of the user as they step down onto the device, but soft enough to allow the user to stand comfortably on the device for minutes at a time. As an example, rigid base 120 may be comprised of a soft rubber material. As another example, rigid base 120 may be comprised of a silicon material.

Rigid base 120 may be available in multiple sizes to account for different sizes of feet. As an example, rigid base 120 may come in a small size, a medium size, and a large size. As an example, rigid base 120 may be approximately 21.5 centimeters in length, approximately 9 centimeters in width, and approximately 2.5 centimeters in height, at the base's highest point. Length is measured from lateral edge 104 to medial edge 106. Width is measured from proximal edge 102 to the distal edge. Height is measured from the bottom surface to the top surface.

In the embodiment shown, top surface of rigid base 120 comprises a sloping contour 103. Sloping contour 103 is configured to receive the four lateral toes of the user and increase in thickness as sloping contour 103 continues from lateral edge 104 of rigid base 120 to median edge 106 of rigid base 120. As an example, at its lowest point sloping contour 103 may be at a height of approximately 5 millimeters and at its highest point sloping contour 103 may be at a height of approximately 25 millimeters. In this way, sloping contour 103 is designed to stretch the distal transverse arch, the adductor hallucis transverse and oblique heads, and the flexor hallucis brevis. In order to provide desired stretching, the height of sloping contour 103 may be adjusted to account for the anatomy of different users. For example, sloping contour 103 may have a height between 1 millimeter and 10 millimeters at the lowest point and a height between 10 millimeters and 50 millimeters at the highest point.

As shown in FIG. 1, the bottom surface of rigid base 120 is ovate. In some embodiments the bottom surface of rigid base 120 may sit flat on the ground. An ovate bottom surface allows the user to perform different therapeutic exercises as the user can performing a rocking motion while pressing their foot onto the top surface of rigid base 120.

The top surface of rigid base 120 comprises a toe retention arrangement, such as depression 122 near medial edge 106 of rigid base 120. Other toe retention arrangements may be utilized (in isolation or in combination), such as a retaining strap. Depression 122 is configured to receive the big toe of the user. As an example, the rigid base 120 may be at a height of approximately 5 millimeters on the portion of the base that contains depression 122. As an example, the width of depression 122 may be approximately 40 millimeters and the depth of depression 122 may be approximately 30 millimeters. The lateral edge of depression 122 may be contoured to comfortably fit the user's big toe. Depression 122 may assist with stretching the fascia that stretches from the heel to the big toe. Depression 122 may assist with both vertical and horizontal stretching of the big toe, allowing the user to more effectively activate the hallucis muscles of the big toe separately from the other muscles of the foot. Other depression sizes may be necessary to accommodate the anatomy of different users, for example, a width between 10 millimeters and 80 millimeters and a depth between 10 millimeters and 30 millimeters.

As shown in FIG. 1, proximal edge 102 of rigid base 120 is curved to conform to the distal edge of the foot.

Lateral edge 104 of rigid base 120 includes lateral connection arrangement 108. Medial edge 106 of rigid base 120 includes a medial connection arrangement 116. As an example, medial connection arrangement 116 may comprise two holes in medial edge 106 of rigid base 120 and lateral connection arrangement 108 may comprise four holes in lateral edge 104 of rigid base 120. As an example, the holes of the connection arrangements may each be approximately 10 millimeters long and 3 millimeters wide. In an alternative embodiment, medial connection arrangement 116 may be absent, or a different number of holes may be used in either lateral or medial connection arrangements.

Lateral connection arrangement 108 is configured to receive a first lateral adjustable toe retainer 112 and a second lateral adjustable toe retainer 114. As shown in FIG. 1, lateral adjustable toe retainers 112 and 114 each comprise a strap which enters and exits through lateral connection arrangement 108 and is configured to wrap around a toe of the user. First lateral adjustable toe retainer 112 is configured to wrap around and stretch the fifth toe, and second lateral adjustable toe retainer 114 is configured to wrap around and stretch the fourth toe. Stretching the fourth and fifth toes may assist with engaging the stabilizing muscles in the feet and alleviating tightness in the muscles of the foot. Other configurations of applying retainers to the toes are possible, for example, wrapping straps around the third and fourth toe. When engaged with a toe, lateral adjustable toe retainer 112 or 114 abducts the toe from the foot and may rotate the toe outward in respect to the midline of the body. The strap comprises a material that is sufficiently inelastic to hold the toe in the desired position, but soft enough to allow for the user to comfortably wear the device for minutes at a time. As an example, the strap may be comprised of a polyester material, such as nylon webbing.

Medial connection arrangement 116 is configured to receive a medial adjustable toe retainer 118. As shown in FIG. 1, medial adjustable toe retainer 118 comprises a strap which enters and exits through medial connection arrangement 116 and is configured to wrap around a toe of the user. When engaged with a toe, medial adjustable toe retainer 118 adducts the toe from the foot and may rotate the toe toward the midline of the body. The strap comprises a material that is sufficiently inelastic to hold the toe in the desired position, but soft enough to allow for the user to comfortably wear the device for minutes at a time. As an example, the strap may be comprised of a polyester material, such as nylon webbing.

Lateral adjustable toe retainers 112 and 114 and medial adjustable toe retainer 118 are adjustable to allow the user to tighten or loosen the retainer to a setting that fits the size of the user's foot and stretches the toes in an optimal way for the specific user's need. In some embodiments, the ends of the strap of lateral adjustable toe retainers 112 and 114 may be configured to removably connect. In some embodiments, the straps of medial adjustable toe retainer 118 may be configured to removably connect. As an example, the straps may comprise Velcro on at least a portion of the strap.

Differing numbers of adjustable toe retainers may be used. For example, in some embodiments there may be only one, or at least three lateral adjustable toe retainers.

In some embodiments, therapeutic footwear device 100 may include a medial cavity 126 on the top surface or bottom surface on medial edge 106 of rigid base 120. In some embodiments, therapeutic footwear device 100 may also include a lateral cavity 124 on the top surface or bottom surface of lateral edge 104 of rigid base 120. Because the adjustable toe retainers adjust to fit the needs of each user, there may be a portion of the strap that hangs over the edge of rigid base 120. Cavities 124 and 126 may be configured to house the excess of the straps of the adjustable toe retainers in order to prevent the straps from dragging on the ground. As an example, cavities 124 and 126 may each comprise a portion of Velcro for the excess of the straps to connect to. As another example, cavities 124 and 126 may each comprise an opening for the excess of the straps to feed into.

As shown in FIGS. 2-8, therapeutic footwear device 200 comprises a rigid platform 202 configured to receive the distal portion of a foot 300. Rigid platform 202 comprises a top surface and a bottom surface. As an example, rigid platform 202 may be generally rectangular in shape. As an example, rigid platform 202 may be approximately 20 centimeters in width and approximately 15 centimeters in length. In some embodiments, rigid platform 202 is designed to maintain equal force on foot 300 and allow the user to perform closed kinetic chain exercises. While a device for a user's right foot is depicted, a mirror-image device for a user's left foot is contemplated and may also be utilized.

Rigid platform 202 is comprised of a material hard enough to resist permanent deformation under the weight of the user as they step down onto the device, but soft enough to allow the user to stand comfortably on the device for minutes at a time. As an example, rigid platform 202 may be comprised of a polycarbonate material.

As shown in FIGS. 2-5 and 7-8, therapeutic footwear device 200 comprises a lateral side wall 204 and a medial side wall 206 that extend upwards from the top surface of rigid platform 202. Lateral side wall 204, medial side wall 206, and rigid base 202 may be constructed as one solid piece, or they may be constructed as separate pieces which are then joined together. As an example, lateral side wall 204 and medial side wall 206 may be joined to rigid platform 202 by epoxy or another adhesive.

Lateral side wall 204 and medial side wall 206 may be comprised of the same or similar material as rigid platform 202. As an example, lateral side wall 204 and medial side wall 206 may be comprised of a polycarbonate material.

Figure 2:
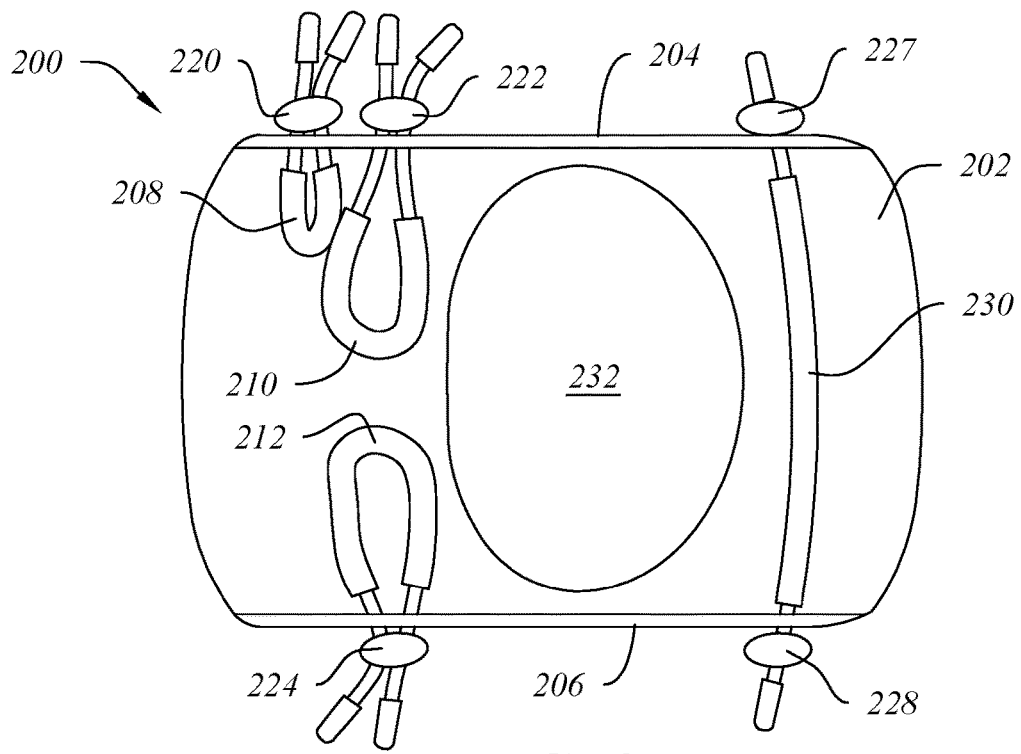
FIG. 2 shows a top view of an embodiment of a therapeutic foot and ankle alignment device in accordance with one embodiment of the invention.
Figure 3:
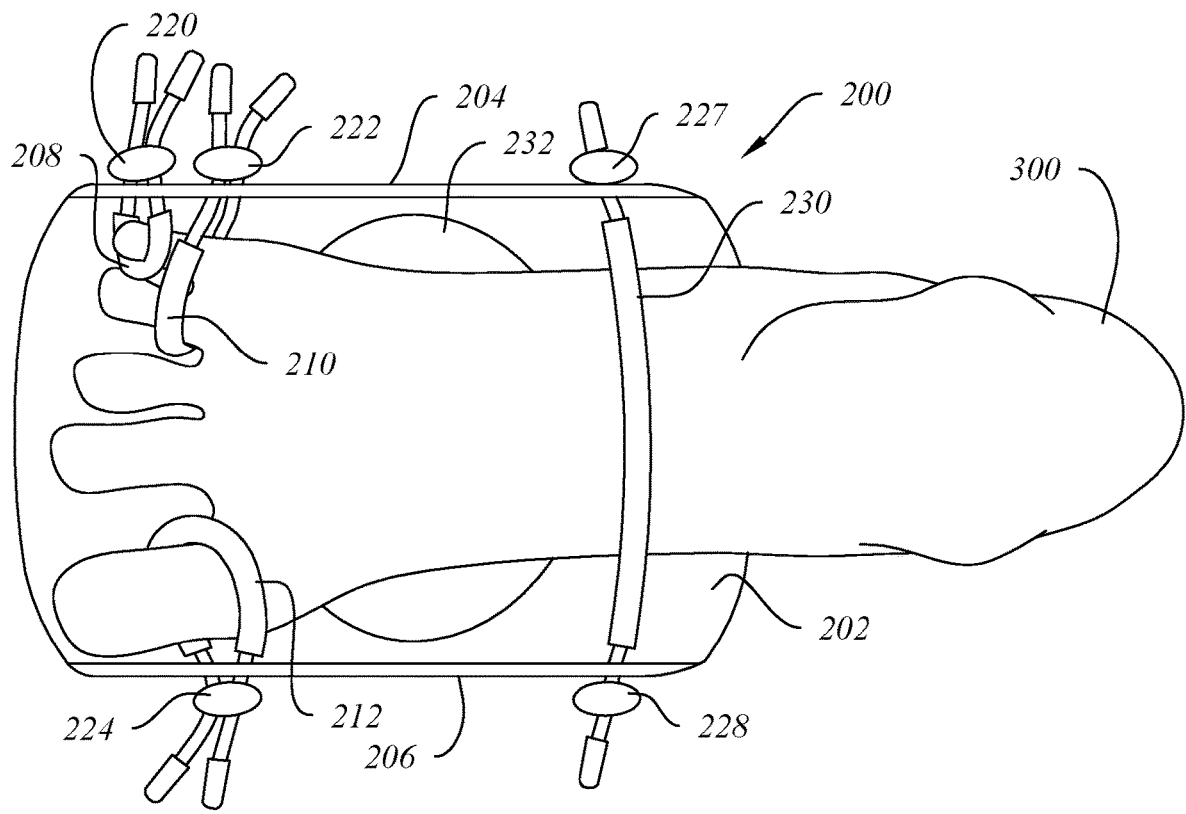
FIG. 3 shows a top view of the therapeutic foot and ankle alignment device with a user's foot inserted, in accordance with one embodiment of the invention.

As shown in FIGS. 2 and 3, lateral side wall 204 is substantially parallel to the lateral side of foot 300 and medial side wall 206 is substantially parallel to the medial side of foot 300. As an example, lateral side wall 204 and medial side wall 206 may extend approximately the length of rigid platform 202 and may be approximately 5 centimeters in height.

Figure 5:
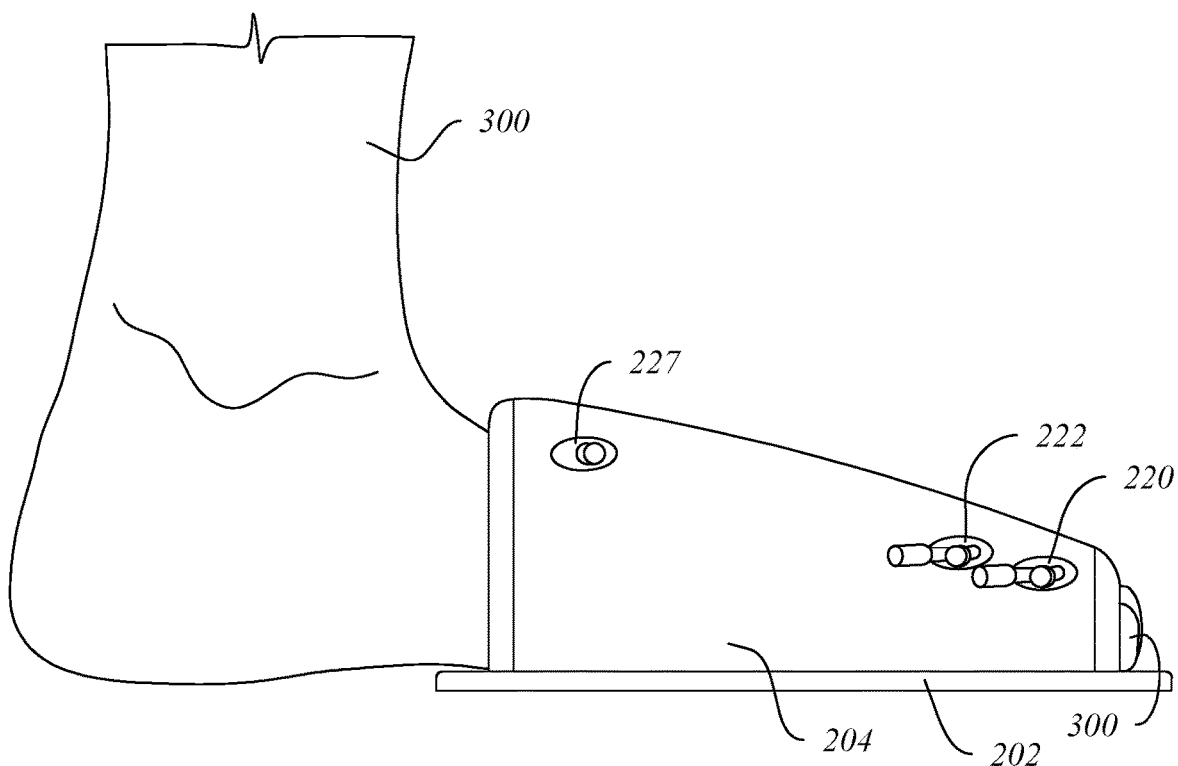
FIG. 5 shows a lateral side view of the therapeutic foot and ankle alignment device from FIG. 2 with a user's foot inserted in accordance with one embodiment of the invention.
Figure 6:
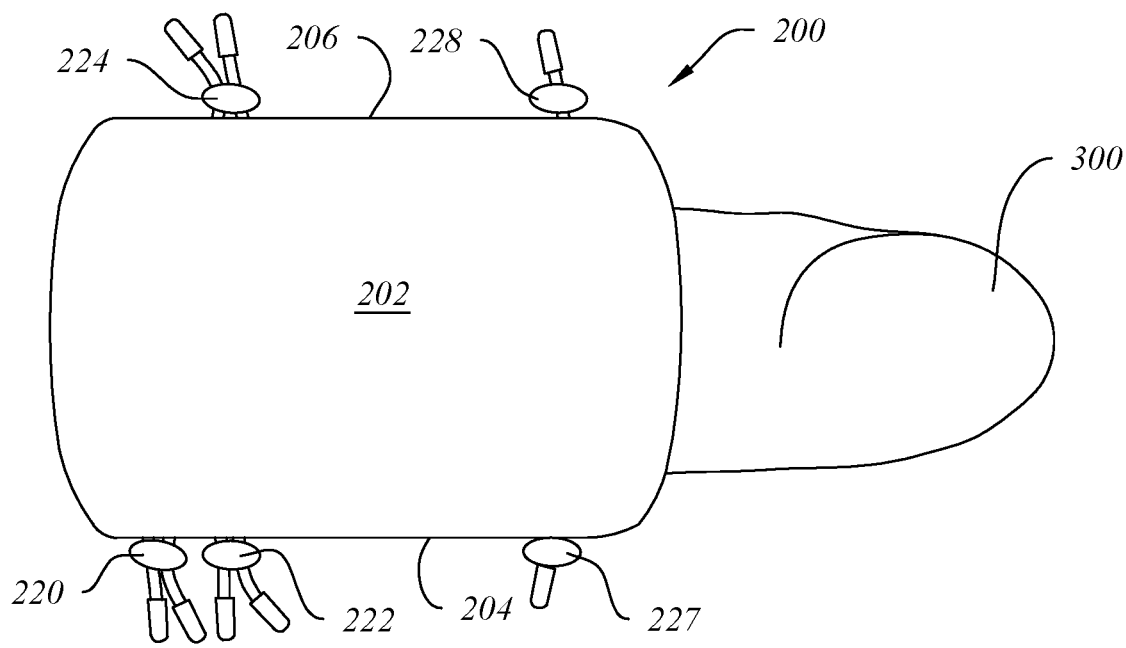
FIG. 6 shows a bottom view of the therapeutic foot and ankle alignment device from FIG. 2 with a user's foot inserted in accordance with one embodiment of the invention.
Figure 8:
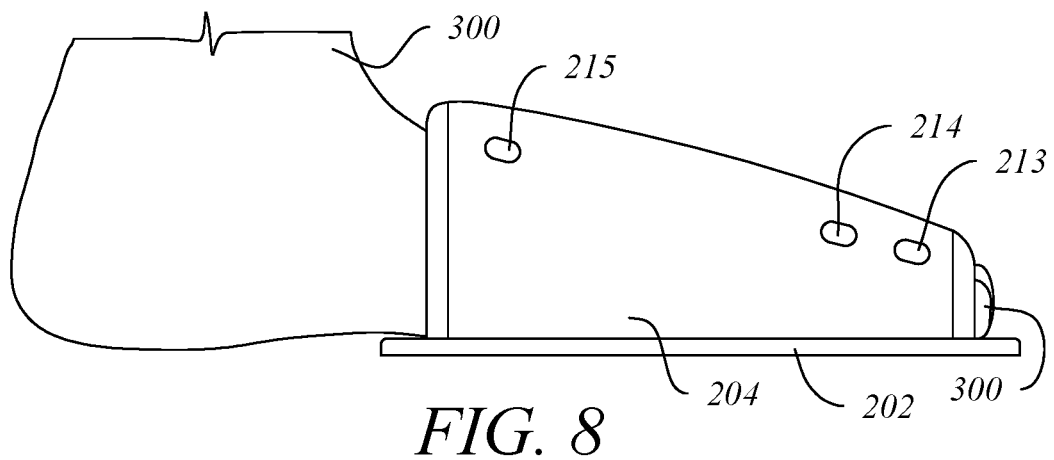
FIG. 8 shows a lateral side view of the therapeutic foot and ankle alignment device from FIG. 2 with a user's foot inserted in accordance with one embodiment of the invention with the adjustable foot retainer, adjustable toe retainers, and adjustable fasteners omitted.

As shown in FIGS. 5 and 8, lateral side wall 204 of rigid platform 202 comprises three lateral connection arrangements: a proximal lateral connection arrangement 215, a primary distal lateral connection arrangement 213, and an alternate distal lateral connection arrangement 214. Lateral connection arrangements 213, 214, and 215 each comprise a hole (occluded in FIG. 5 by fasteners 220, 222, and 227) in lateral side wall 204 of rigid platform 202. In some embodiments (not shown) a different number of holes may be used. For example, two holes may be used.

Figure 4:
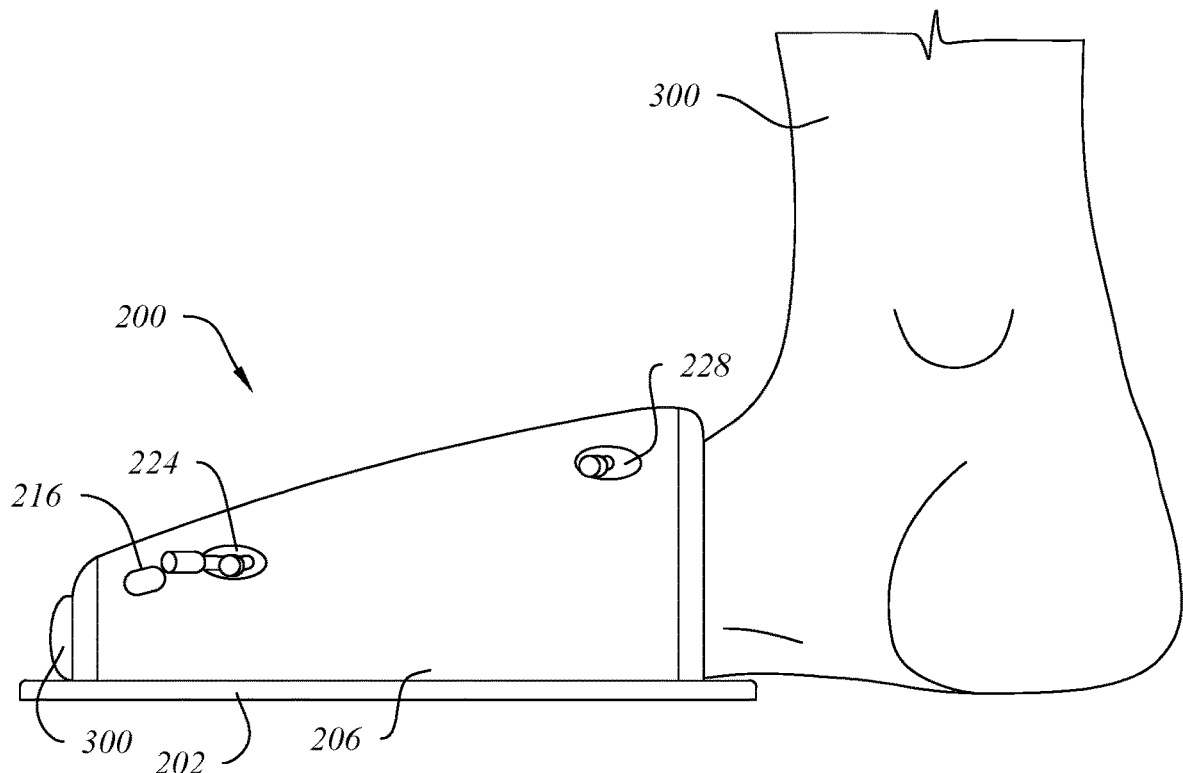
FIG. 4 shows a medial side view of the therapeutic foot and ankle alignment device with a user's foot inserted in accordance with one embodiment of the invention.
Figure 7:
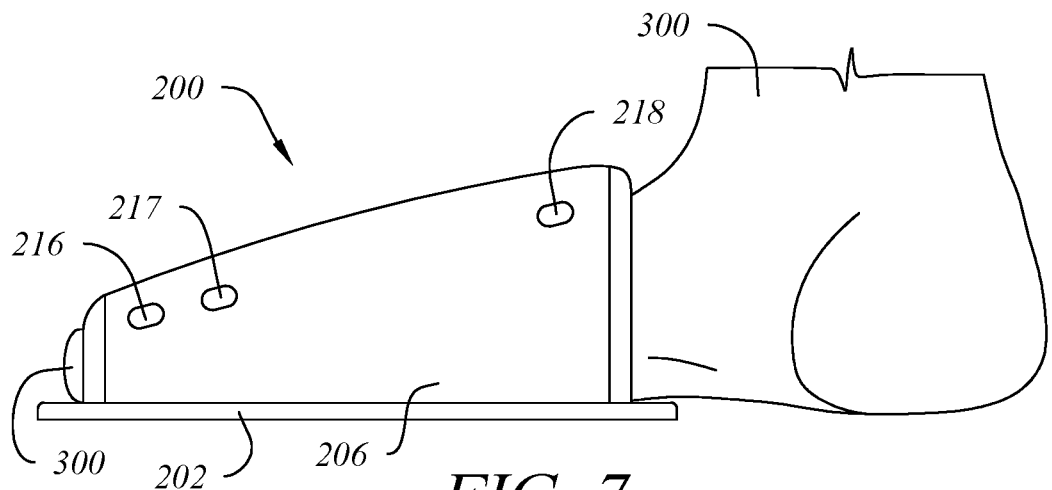
FIG. 7 shows a medial side view of the therapeutic foot and ankle alignment device from FIG. 2 with a user's foot inserted in accordance with one embodiment of the invention with the adjustable foot retainer, adjustable toe retainers, and adjustable fasteners omitted.

As shown in FIGS. 4 and 7 medial side wall 206 of rigid platform 202 includes three medial connection arrangements: a proximal medial connection arrangement 218, a primary distal medial connection arrangement 216, and an alternate distal medial connection arrangement 217. Medial connection arrangements 216, 217, and 218 each comprise a hole (occluded in FIG. 4 by fasteners 224 and 228) in medial side wall 206 of rigid platform 202. In some embodiments (not shown) a different number of holes may be used.

In some embodiments, lateral side wall 204 may include as few as one, or as many as five lateral connection arrangements.

In some embodiments, medial side wall 206 may include as few as one, or as many as five medial connection arrangements.

As shown in FIGS. 2-6, adjustable foot retainer 230 is located on the proximal end of therapeutic footwear device 200. Adjustable foot retainer 230 comprises a strap adapted to secure foot 300 to rigid base 202. The strap is comprised of a material that is sufficiently inelastic to hold foot 300 in place, but soft enough to allow for the user to comfortably wear the device for minutes at a time. As an example, the strap may be comprised of a polyester material.

The strap of adjustable foot retainer 230 is configured to enter through proximal lateral connection arrangement 215 on lateral wall 204 and exit through proximal medial connection arrangement 218 on medial wall 206, or vice versa.

One end of the strap of adjustable foot retainer 230 passes through a first adjustable fastener 227 and the opposite end of the strap of adjustable foot retainer 230 passes through a second adjustable fastener 228. Adjustable fasteners 227 and 228 are configured to allow the user to tighten or loosen the strap to secure foot 300 to rigid base 202. As an example, adjustable fasteners 227 and 228 may each comprise a cord lock that attaches to the strap of adjustable foot retainer 230 so that when the cord lock is squeezed together, tension is released and the cord lock can move freely up and down the strap.

In some embodiments one end of the strap of adjustable foot retainer 230 may be fixed to either medial side wall 206 or lateral side wall 204. The end of the strap of adjustable foot retainer 230 that is not secured to medial side wall 206 or lateral side wall 204 may pass through adjustable fastener 227 or 228 configured to allow the user to tighten or loosen the strap to secure foot 300 to rigid base 202. Some embodiments may not include an adjustable foot retainer.

As shown in FIGS. 2-3 and 5-6, a first lateral adjustable toe retainer 208 and a second lateral adjustable toe retainer 210 are located on the distal end of lateral side wall 204. Lateral adjustable toe retainers 210 and 208 are configured to wrap around the fourth and fifth toes, respectively.

Stretching the fourth and fifth toes may assist with engaging the stabilizing muscles in the feet and alleviating tightness in the muscles of the foot.

As shown in FIGS. 2-4 and 6, medial adjustable toe retainer 212 is located on the distal end of medial side wall 206. Medial adjustable toe retainer 212 is configured to wrap around and stretch the big toe. Stretching the big toe may assist with alleviating tightness in the fascia of the foot.

Adjustable toe retainers 208, 210, and 212 each comprise a strap configured to wrap around the toe(s) of the user. The straps are comprised of a material that is rigid enough to hold the toe(s) in place, but soft enough to allow for the user to comfortably wear the device for minutes at a time. As an example, the straps may be comprised of a polyester material.

Lateral adjustable toe retainers 208 and 210 are adjustable to allow the user to tighten or loosen the retainers to a setting that fits the size of the user's foot and abduct the toes in an optimal way for the specific user's need. The ends of the strap of first lateral adjustable toe retainer 208 pass through primary distal lateral connection arrangement 213 and a first lateral adjustable fastener 220. First lateral adjustable fastener 220 comprises a cord lock that attaches to the strap so that when the cord lock is squeezed together, tension is released and the cord lock can move freely up and down the strap. The ends of the strap of second lateral adjustable toe retainer 210 pass through alternate distal lateral connection arrangement 214 and a second lateral adjustable fastener 222. Second lateral adjustable fastener 222 comprises a cord lock that attaches to the strap so that when the cord lock is squeezed together, tension is released and the cord lock can move freely up and down the strap. As will be apparent to one of skill in the art, other locking mechanisms may be used to hold the straps in place. Some embodiments may comprise as few as one, or as many as four lateral adjustable toe retainers.

Medial adjustable toe retainer 212 is adjustable to allow the user to tighten or loosen the retainer to a setting that fits the size of foot 300 and abduct the toes in an optimal way for the specific user's need. The ends of the strap of medial adjustable toe retainer 212 pass through alternate distal medial connection arrangement 217 and a medial adjustable fastener 224. Medial adjustable fastener 224 comprises a cord lock that attaches to the strap so that when the cord lock is squeezed together, tension is released and the cord lock can move freely up and down the strap.

There may be elevating inserts located on adjustable toe retainers 208, 210, or 212. The elevating inserts may be designed to lift the toes of the user upwards to stretch the stabilizing muscles of the foot. As an example, adjustable toe retainers 208, 210, and 212 may comprise an elevating insert located on the portion of the strap that rests on the bottom surface of the user's toe. As an example, the elevating insert may be approximately 2 centimeters in thickness. As an example, the insert may be made of a soft rubber material.

Therapeutic footwear device 200 may include a padded cushion 232 on the top surface of rigid platform 202. Padded cushion 232 may make the device more comfortable to wear for extended periods or may assist in holding foot 300 in place while using the device.

The device may be used to teach and train the user to properly activate hard to reach stabilizing muscles in the foot. The device may be used to improve form during common exercise movements such as squats. The device may also be used to warm up the body before physical activity. The device may also be used to decrease pain and rehabilitate injuries.

The device may be placed under the foot of the user. The toes may be secured using the adjustable toe retainers so that the toes are abducted from the foot. While wearing the device, the user may perform isometric contractions or any single kinematic motion or combination of kinematic motions of the toes in alternating movement patterns while sitting, laying down, or standing. The user may also walk or ambulate while wearing the device. The user may also wear the device passively, without performing any movements to stretch the muscles in the foot.

The use of the device may result in an isometric tensioning of the fascia to align and realign misappropriated tension spots, trigger points, pain points, and stress points in the body.

The use of the device may activate the inner fascial connections of the stabilizing muscles and use that pathway to transmit force up the body from the foot. The use of the device may strengthen the arch of the foot. The device is adjustable to accommodate different users. The device's adjustability also allows users to vary the type and depth of stretch being performed.

At least one embodiment is disclosed and variations, combinations, and/or modifications of the embodiment(s) and/or features of the embodiment(s) made by a person having ordinary skill in the art are within the scope of the disclosure. For example, while exemplary embodiments for a device to be used with a user's right foot may be shown, a mirror-image embodiment for a user's left foot may also be utilized. Alternative embodiments that result from combining, integrating, and/or omitting features of the embodiment(s) are also within the scope of the disclosure. The feature or features of one embodiment may be applied to other embodiments to achieve still other embodiments, even though not described, unless expressly prohibited by this disclosure or the nature of the embodiments. The scope of protection is not limited by the description set out above but is defined by the claims that follow, the scope including all equivalents of the subject matter of the claims. Each and every claim is incorporated as further disclosure into the specification and the claims are embodiment(s) of the present invention.

The claimed invention is:

1. A therapeutic footwear device comprising:
   a rigid base configured to receive the distal portion of a foot comprising a top surface, a bottom surface, a lateral edge, a medial edge, a proximal edge, and a distal edge;
   the top surface of the rigid base comprising a sloping contour, wherein the contour is configured to receive the four lateral toes and increases in thickness as the contour continues from the lateral edge to the medial edge of the rigid base and wherein a lateral connection arrangement is disposed upon the sloping contour adjacent to the lateral edge of the rigid base;
   a medial toe retention arrangement adapted to prevent a user's first toe from moving towards the lateral edge of the rigid base;
   a lateral adjustable toe retainer connected to the lateral connection arrangement adjacent to the lateral edge of the rigid base; and
   wherein the lateral adjustable toe retainer is adapted to abduct at least one of the user's fourth and fifth toes along the sloping contour toward the lateral edge of the rigid base.

2. The therapeutic footwear device of claim 1, wherein the medial toe retention arrangement comprises a depression near the medial edge of the rigid base.

3. The therapeutic device of claim 2, wherein the depression comprises a substantially vertical surface dividing the depression from the lateral portion of the device.

4. The therapeutic footwear device of claim 1, wherein the medial toe retention arrangement comprises a medial connection arrangement on the medial edge of the rigid base and a medial adjustable toe retainer connected to the medial connection arrangement on the medial edge of the rigid base.

5. The therapeutic footwear device of claim 4, wherein the bottom surface of the rigid base is substantially ovate.

6. The therapeutic footwear device of claim 5, wherein the medial adjustable toe retainer comprises a strap which enters and exits through the medial connection arrangement on the medial edge.

7. The therapeutic footwear device of claim 6, wherein the lateral adjustable toe retainer comprises a strap which enters and exits through the lateral connection arrangement adjacent to the lateral edge.

8. The therapeutic footwear device of claim 7, wherein the medial connection arrangement on the medial edge comprises a hole in the medial edge.

9. The therapeutic footwear device of claim 8, wherein the lateral connection arrangement adjacent to the lateral edge comprises a hole in the lateral edge.

10. The therapeutic device of claim 9, wherein the bottom surface of the rigid base further comprises a cavity on the lateral edge configured to house the excess of the strap of the lateral adjustable toe retainer.

11. The therapeutic device of claim 10, wherein the bottom surface of the rigid base further comprises a cavity on the medial edge configured to house the excess of the strap of the medial adjustable toe retainer.

12. The therapeutic device of claim 11, wherein the device further comprises at least one additional lateral adjustable toe retainer attached to the lateral connection arrangement.

13. The therapeutic device of claim 4, wherein the medial adjustable toe retainer is adapted to adduct at least one of the user's toes.

14. The therapeutic device of claim 13, wherein the medial toe retention arrangement further comprises a depression near the medial edge of the rigid base and wherein the depression comprises a substantially vertical surface dividing the depression from the lateral portion of the device.

15. The therapeutic device of claim 1, wherein the sloping contour is shaped such that the device stretches at least one of the user's distal transverse arch, the user's adductor hallucis transverse and oblique heads, and the user's flexor hallucis brevis.

16. The therapeutic device of claim 15, wherein the sloping contour is shaped such that the device stretches the user's distal transverse arch.

17. The therapeutic device of claim 1, wherein the proximal edge of the rigid base is curved to conform to the user's proximal phalanges.

18. The therapeutic device of claim 1, wherein the lateral adjustable toe retainer is comprised of a plurality of straps wherein a first strap is configured to abduct the user's fourth toe and a second strap is configured to abduct the user's fifth toe.

19. A therapeutic footwear device comprising:
a rigid base, configured to receive the distal portion of a foot, the rigid base comprising a top surface, a bottom surface, a lateral edge, and a medial edge, wherein the bottom surface of the rigid base is substantially ovate;
the top surface of the rigid base comprising a sloping contour, wherein the contour is configured to receive the four lateral toes and increases in thickness as the contour continues from the lateral edge to the medial edge of the rigid base and wherein the contour further comprises a lateral connection arrangement comprising at least one hole near the lateral edge of the rigid base;
the top surface of the rigid base further comprising a depression near the medial edge of the rigid base;
a medial connection arrangement comprising a hole along the medial edge of the rigid base;
a lateral adjustable toe retainer which comprises a strap that enters and exits through the hole near the lateral edge of the rigid base, both ends of the strap configured to removably connect;
wherein the lateral adjustable toe retainer is adapted to abduct at least one of the user's fourth and fifth toes along the sloping contour;
a medial adjustable toe retainer which comprises a strap that enters and exits through the hole along the medial edge of the rigid base, both ends of the strap configured to removably connect;
the bottom surface of the rigid base further comprising a cavity on the lateral edge configured to house the excess of the strap of the lateral adjustable toe retainer and a cavity on the medial edge configured to house the excess of the strap of the medial adjustable toe retainer.

* * * * *